(12) United States Patent
Marincak

(10) Patent No.: US 6,201,623 B1
(45) Date of Patent: *Mar. 13, 2001

(54) SURFACE TOPOGRAPHY ENHANCEMENT

(75) Inventor: Anton Marincak, Stittsville (CA)

(73) Assignee: National Research Council of Canada, Ottawa (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,055
(22) PCT Filed: Feb. 14, 1995
(86) PCT No.: PCT/CA95/00070
  § 371 Date: Aug. 8, 1997
  § 102(e) Date: Aug. 8, 1997
(87) PCT Pub. No.: WO96/25659
  PCT Pub. Date: Aug. 22, 1996
(51) Int. Cl.[7] .................................................. G02B 26/08
(52) U.S. Cl. ........................................... 359/196; 359/197
(58) Field of Search .................................... 359/196, 197, 359/201, 202, 900; 358/474, 475, 483, 494, 497; 356/445, 446

(56) References Cited

U.S. PATENT DOCUMENTS

| 4,863,268 | * | 9/1989 | Clarke et al. | 356/237 |
| 4,900,153 | * | 2/1990 | Weber et al. | 356/430 |
| 4,920,385 | | 4/1990 | Clarke et al. . | |

FOREIGN PATENT DOCUMENTS 2133 871  *  8/1984  (GB) .

* cited by examiner

Primary Examiner—James Phan
(74) Attorney, Agent, or Firm—Marks & Clerk

(57) ABSTRACT

An apparatus for producing a topographically enhanced representation of an object, comprises a light source for generating a light beam for illuminating the object. The light beam has a zone where the intensity falls off rapidly with distance away from the beam. The object is scanned at a grazing angle of about 3 to 6° in this zone as the light beam is progressively moved over the object.

11 Claims, 6 Drawing Sheets

Figure 1:
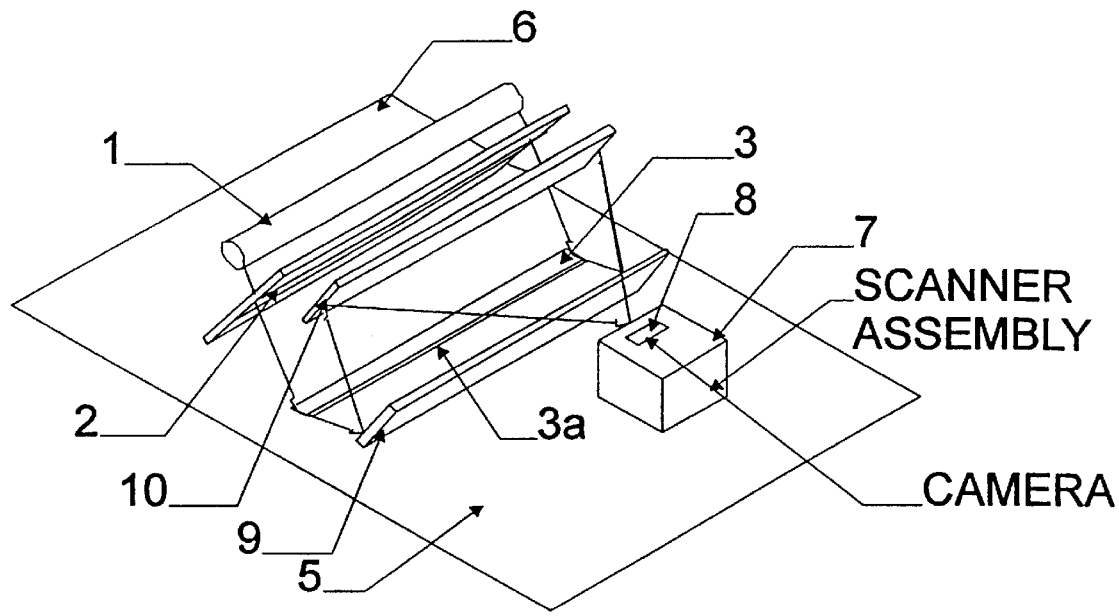

A = ILLUMINATION ANGLE
B = GRAZING ANGLE

SURFACE TOPOGRAPHY ENHANCEMENT

This invention relates to surface topography enhancement, and more particularly to a method and apparatus for producing a topographically enhanced representation of an object.

Many imaging systems are known for producing a representation of the surface of the object. The simplest of such systems would be a photocopier, for example, where the object is illuminated to form a latent image on a selenium drum. Optical scanners for scanning images into computers are well known.

The problem with such systems is that they do not make good representations of topographically rich surfaces, the two-dimensional nature of such systems inherently being ill-suited to the reproduction of topographical detail.

U.S. Pat. No. 4,920,385 discloses an apparatus for inspecting surface flaws wherein the surface is scanned with a moving light beam. However, this apparatus does not provide the desired resolution of topological features.

An object of the present invention is to provide a system capable of enhancing the representation of topographical detail in a two-dimensional image.

According to the present invention there is provided an apparatus for producing a topographically enhanced representation of an object, comprising a light source for generating a band of light for illuminating the object, said band of light defining an edge zone of finite width due to diffraction effects with an intensity profile that falls off rapidly with distance in a transverse direction relative to said band of light, said finite width being sufficient to accommodate an image strip; an arrangement for progressively advancing said band of light over the object in said transverse direction; and means for scanning said object at a grazing angle along said image strip within said edge zone as said band of light progressively advances over said object.

By "falls of rapidly" is meant that the change of intensity is similar to that experienced in the edge zone of a collimated band of light from a slit, although it can be generated by other means. Typically this change in intensity is in the order of a factor of two over a distance of about 0.08 inches. In such an embodiment, the surface to be inspected is illuminated by a light source which produces a collimated band of light from a slit bounded by an edge zone where diffraction effects are noticeable. Along either edge of this band the intensity drops off rapidly as the distance from the edge increases.

This area or strip is the edge-of-light zone resulting from diffraction from the edges of the slit. Its width is very narrow but finite and its characteristics can be modified by changing the angle of the illumination source. An image strip focused on the surface at a grazing angle of preferably 3 to 6 degrees in this zone is used to gather the intensity changes caused by slope changes on the surface. Small changes in slope cause large shifts in light intensity.

A line scanner is preferably used to collect the intensity data. The image strip normally has a width of only a pixel or two roughly measured to be 0.001 in. This easily fits into the edge-of-light zone used in the scanner, which has a zone width close to 0.08 in. Depending upon where the strip is located within the zone, the intensity shifts go from high to low or low to high. As the scanner travels along the surface the edge of light moves with it. The enhanced image is constructed by combining the strips together.

The end result is a high resolution image with brighter or darker areas highlighting surface slope changes.

The invention also provides a method of producing a topographically enhanced representation of an object, comprising progressively moving a light beam over the surface of the object, said light beam having a zone whose intensity changes rapidly with distance, and scanning said object at a grazing angle in said zone as the light beam is moved over the surface.

Figure 2:
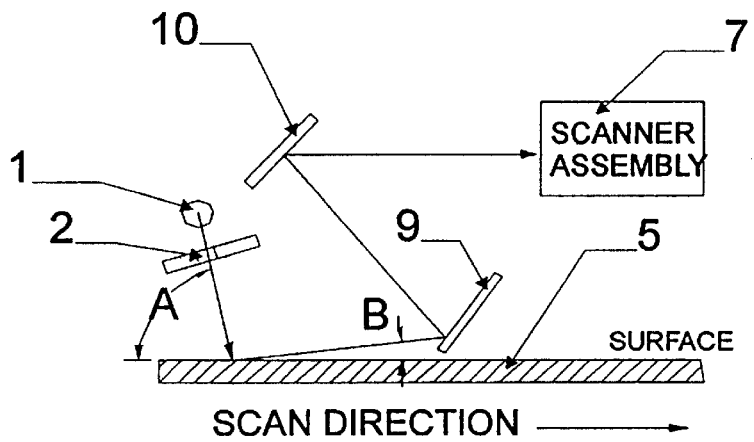
Figure 3:
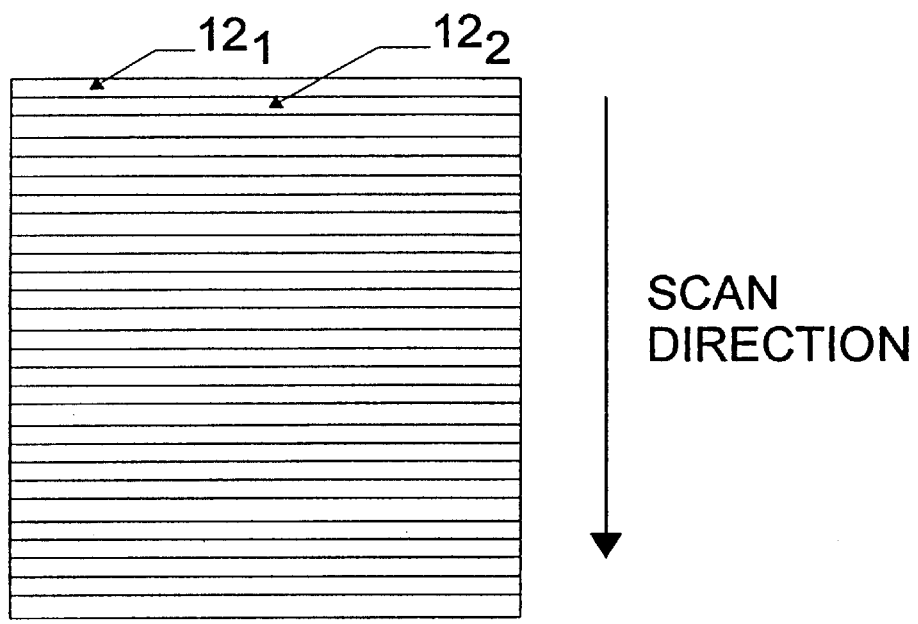
Figure 4:
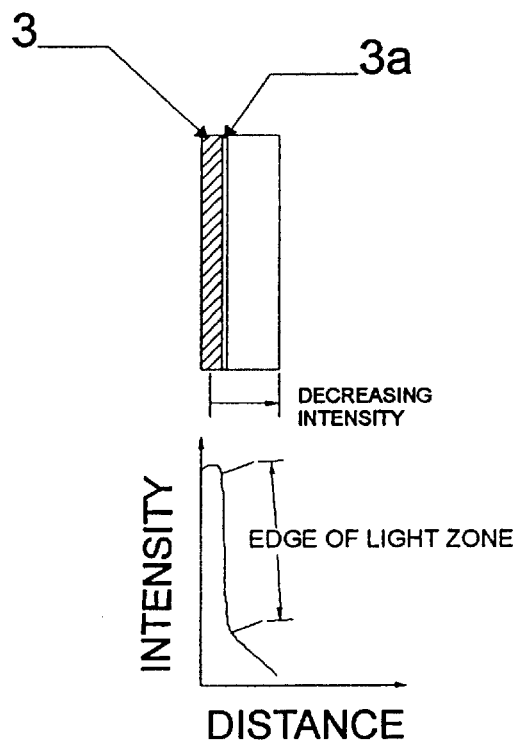
Figure 5:
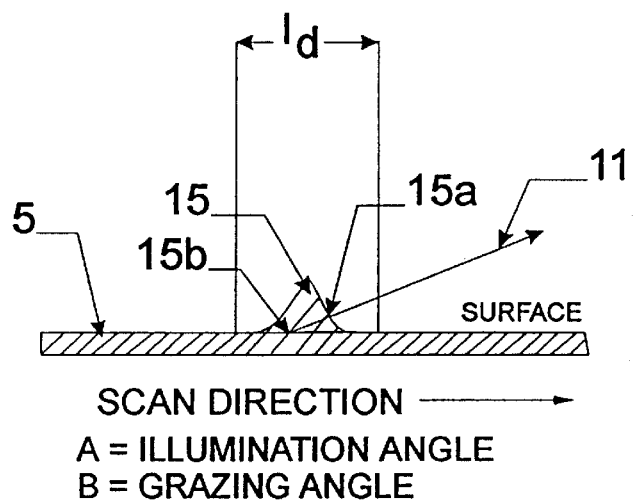
Figure 6:
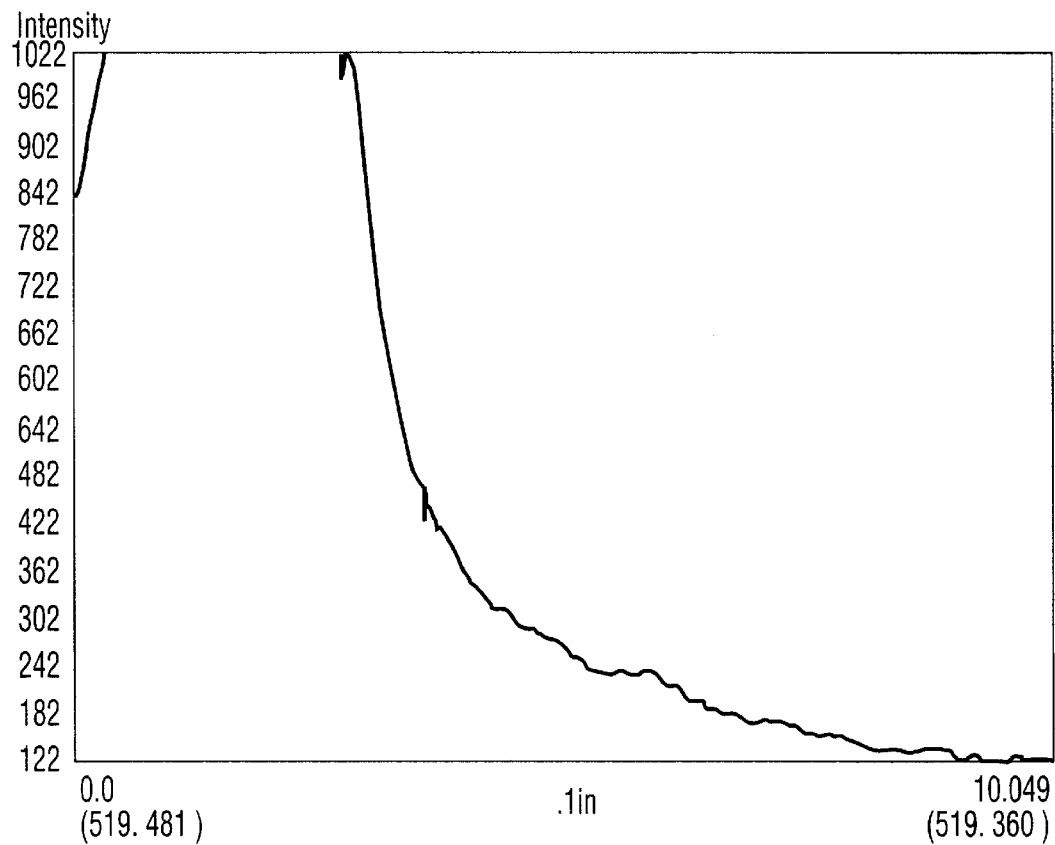
Figure 7:
Figure 8:
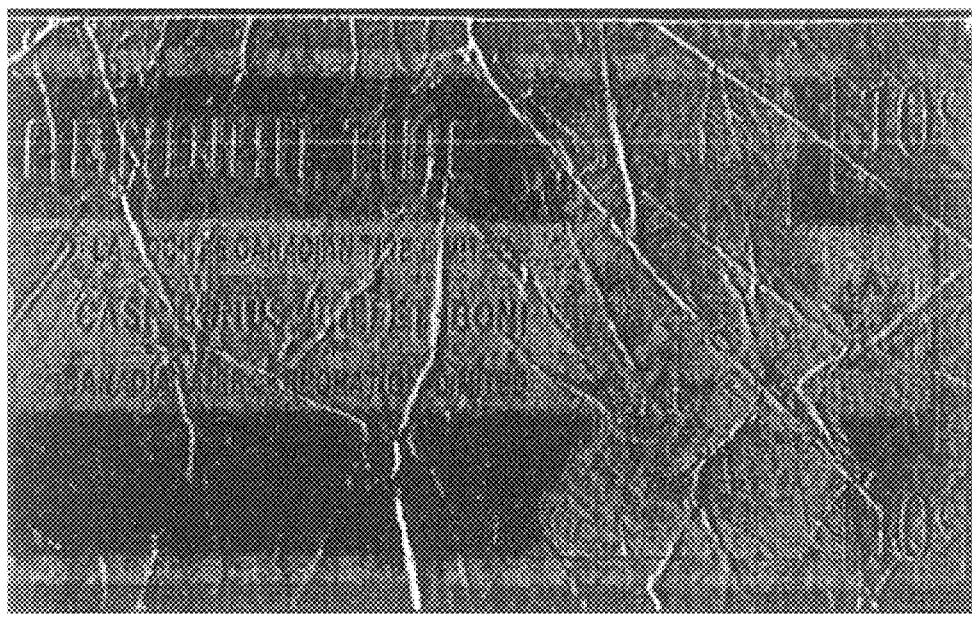
Figure 9:
Figure 10:
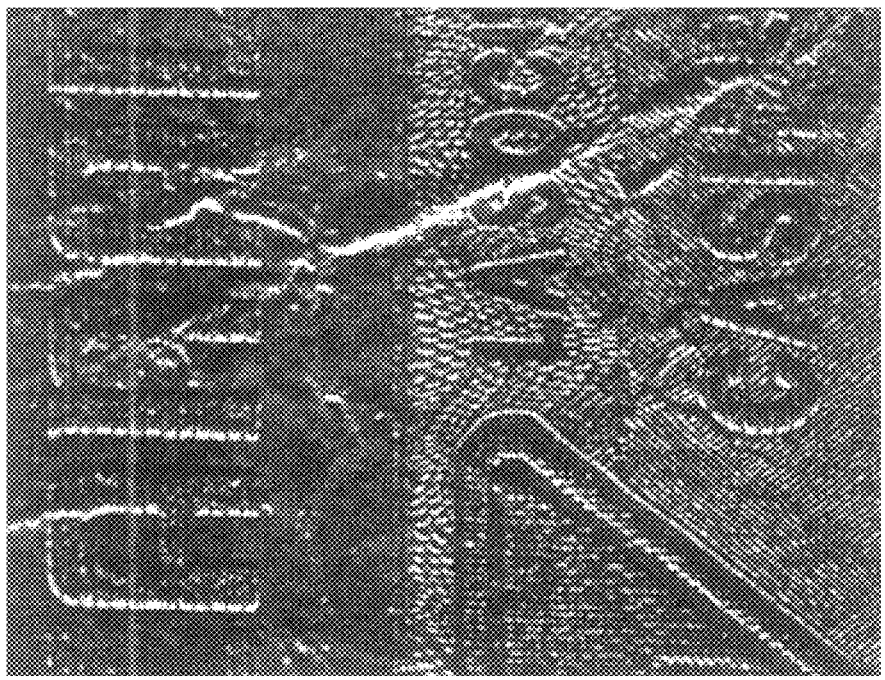
Figure 11:
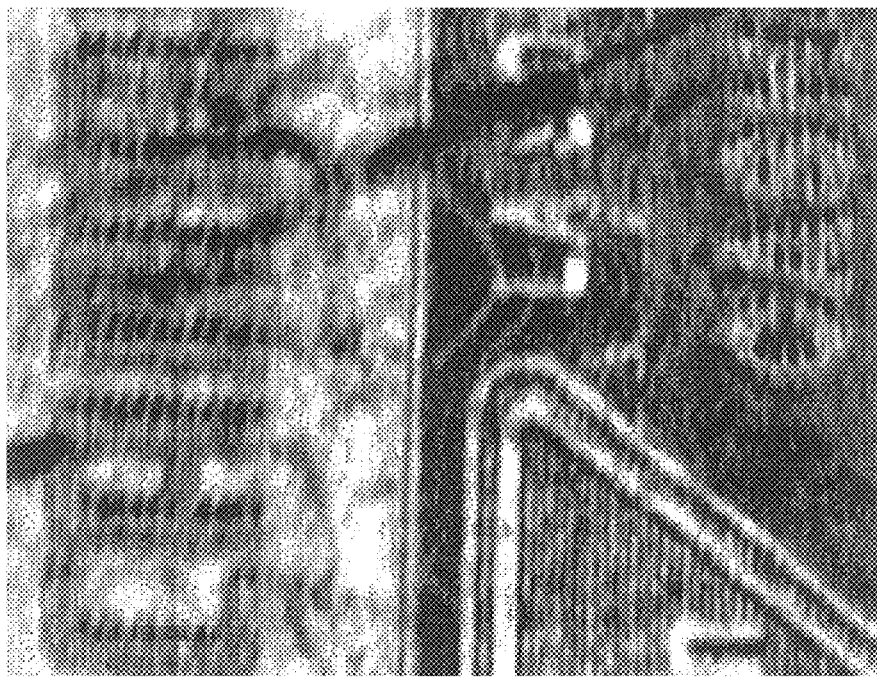

The invention will now be described in more detail, by way of example only, with reference to the accompanying drawings, in which:

FIG. 1 is a perspective view of a simplified optical setup;
FIG. 2 is a sectional view of the simplified optical setup;
FIG. 3 illustrates the image construction;
FIG. 4 shows the edge-of-light zone characteristics;
FIG. 5 illustrates the principle of the invention;
FIG. 6 is an intensity versus distance plot in the edge zone in units of one inch;
FIG. 7 shows Canadian tire money scanned conventionally;
FIG. 8 shows Canadian tire money scanned using an apparatus in accordance with invention set to respond to dark-to-light slope changes.
FIG. 9 shows Canadian tire money scanned using apparatus in accordance with the invention set to respond to light-to-dark slope changes; and
FIGS. 10 and 11 are Close-ups of FIGS. 8 and 9 respectively.

Referring now to FIGS. 1 and 2, the apparatus comprises a light source 1, such as a fluorescent strip lamp, and a rectangular slit 2 through which a collimated beam of light passes and which forms a rectangular band of light 3 on the topographically rich surface 5 of an object 6 to be scanned. Slit 2 is arranged so that the incident light beam strikes the surface at an angle A of about 80°.

The rectangular band has an edge zone 3a in the form of a rectangular strip where the intensity falls of rapidly away from the band. This is the zone where diffraction effects are noticeable.

FIG. 4 shows the profile of the band of light 3 on the surface of the object. In the main zone of the band 3, the light intensity is substantially constant. At the edge, the intensity does not fall to zero immediately due to diffraction effects, although it does fall off very rapidly with distance in an edge zone 3a. In accordance with the invention, the surface is scanned in this edge zone 3a.

Returning to FIGS. 1 and 2, a scanner optics assembly 7 contains a line camera 8 including a charge-coupled device and associated optics for scanning a received image in the edge zone 3a.

Mirrors 9 and 10 are arranged so as to receive light reflected off the surface 5 at a grazing angle B of about 3 to 6° and direct the reflected light to the scanner optics 7.

In operation the arrangement shown in FIGS. 1 and 2 is progressively moved over the surface 5 of the object so that the surface 5 is scanned line by line in the manner shown in FIG. 3 to construct an image made up a series of scan lines in a conventional manner.

Because the surface is scanned at a grazing angle and the intensity changes with distance very rapidly, topograhpical features are enhanced. FIG. 5 shows why. Suppose an otherwise plane surface 5 has a bump 15 lying in the edge zone 3a where the intensity $I_d$ changes very rapidly with distance d. If the scanner optics views the bump in the direction 11, it will see the surface of the bump 15 at point 15a where the intensity has a first value $I_y$. In the absence of the bump 15, it would see the surface at a point 15b where the intensity has a value $I_x$. Since by hypothesis, $(I_x-I_y)$ is substantial due to the rapidly changing intensity with distance d, this shows up in the image as a rapid change in intensity with surface contour.

In order to measure the edge-of-light zone intensity, a National Research Council IPS system was used. The scanner was placed on a semi-transparent surface. The image produced was then digitally captured and analyzed using the image processing software. A calibrated plot of intensity vs distance was produced, as shown in FIG. 6. This shows that the curve has an intensity change of 1022 units to 122 units over a distance of 0.5 inches. The edge-of-light zone on this curve has an intensity change of 1000 units to 422 over a distance of 0.08 inches (1 unit per 0.0001 inch). Many different curves can be generated to suit the surface topography as will be apparent to one skilled in the art. By expanding or condensing the edge-of-light zone the sensitivity to surface topography can be tuned.

FIGS. 7 to 11 show the results obtained with the invention compared with a conventional scan. It will be seen that the invention considerably enhances the surface detail.

I claim:

1. Apparatus for producing a topographically enhanced representation of an object, comprising:
   a) a light source for generating a band of light for illuminating the object, said band of light defining an edge zone of finite width due to diffraction effects with an intensity profile that falls off rapidly with distance in a transverse direction relative to said band of light, said finite width being sufficient to accommodate an image strip;
   b) an arrangement for progressively advancing said band of light over the object in said transverse direction; and
   c) means for scanning said object at a grazing angle along said image strip within said edge zone as said band of light progressively advances over said object.

2. Apparatus as claimed in claim 1, wherein said band of light is projected onto the surface of the object at a near perpendicular angle.

3. Apparatus as claimed in claim 2, wherein said band of light has a main central zone where the intensity is approximately constant, and said edge zone extends on either side of the main central zone.

4. Apparatus as claimed in claim 3, wherein said scanning means comprises means for generating a line image of said object in said edge zone, and a line camera scanning said line image.

5. Apparatus as claimed in claim 4, wherein said edge zone has a width of not more than about two pixels.

6. Apparatus as claimed in claim 4, wherein said line camera includes a charge-coupled device.

7. Apparatus as claimed in claim 1, wherein said light source and said scanning means together form an assembly that is movable over the surface of the object.

8. Apparatus for producing a topographically enhanced representation of an object, comprising:
   a) a light source for generating a band of light for illuminating the object, said band of light defining an edge zone of finite width with an intensity profile that falls off rapidly with distance in a transverse direction relative to said band of light;
   b) an arrangement for progressively advancing said band of light over the object in said transverse direction; and
   c) means for scanning said object at a gazing angle within said edge zone as said band of light progressively advances over said object;
   wherein said grazing angle is 3 to 6°.

9. A method of producing a topographically enhanced representation of an object, comprising the steps of progressively advancing a band of light over the surface of the object, said band of light having an edge zone of finite width due to diffraction effects with an intensity profile that falls off rapidly with distance in a transverse direction relative to said band, said finite width being sufficient to accommodate an image strip, and scanning said object at a grazing angle along said image strip within said edge zone as the light beam advances over the surface.

10. A method as claimed in claim 9, wherein the grazing angle is 3 to 6°.

11. A method as claimed in claim 10, wherein said band of light is projected onto said surface at a near perpendicular angle.

* * * * *